United States Patent
Ishaq (10) Patent No.: US 7,799,348 B2
(45) Date of Patent: *Sep. 21, 2010

(54) THERAPEUTIC COMPOSITION COMPRISING HYALURONIC ACID AND CHONDROITIN SULFATE AND METHOD OF MAKING SAME

(75) Inventor: Suhail Ishaq, Diamond Bar, CA (US)

(73) Assignee: BioCell Technology, LLC, Newport Beach, CA (US)

( * ) Notice: Subject to any disclaimer, the term of this patent is extended or adjusted under 35 U.S.C. 154(b) by 376 days.

This patent is subject to a terminal disclaimer.

(21) Appl. No.: 11/213,260

(22) Filed: Aug. 26, 2005

(65) Prior Publication Data

US 2006/0045920 A1    Mar. 2, 2006

Related U.S. Application Data

(63) Continuation of application No. 10/870,841, filed on Jun. 17, 2004, now Pat. No. 7,091,180, which is a continuation of application No. 10/008,012, filed on Nov. 13, 2001, now Pat. No. 6,780,841.

(51) Int. Cl.
*A61K 34/39* (2006.01)

(52) U.S. Cl. .......................... 424/548; 424/439; 514/2; 514/21; 530/356; 530/407

(58) Field of Classification Search .................. None
See application file for complete search history.

(56) References Cited

U.S. PATENT DOCUMENTS

| | | | |
|---|---|---|---|
| 4,511,653 A | 4/1985 | Play et al. | |
| 4,804,745 A | 2/1989 | Koepff et al. | |
| 5,206,023 A | 4/1993 | Hunziker | |
| 5,364,775 A | 11/1994 | Katsumata et al. | |
| 5,364,845 A | 11/1994 | Henderson | |
| 5,399,347 A | 3/1995 | Trentham et al. | |
| 5,587,363 A | 12/1996 | Henderson | |
| 5,645,851 A | 7/1997 | Moore | |
| 5,840,848 A | 11/1998 | Sturrock et al. | |
| 6,025,327 A * | 2/2000 | Alkayali | 514/2 |
| 6,780,841 B2 * | 8/2004 | Ishaq | 514/2 |
| 7,091,180 B2 * | 8/2006 | Ishaq | 514/2 |

FOREIGN PATENT DOCUMENTS

WO    WO 97 25435    7/1997

OTHER PUBLICATIONS

Desai, B.B. "Handbook of Nutrition and Diet" Illustrated Edition, CRC Press, 2000, pp. 321-323 and 326-330.*
Lagocka et al, "Separation and characteristics of different mucopolysaccharides from bovine trachae cartilage" Food Chemistry, 1997, vol. 60, No. 4, pp. 533-536.*
Altman, R.D. "Rheumatoid Arthritis" The Merck Manuals: Online Medical Library, updated 2008, retrieved on Apr. 2, 2009 from URL: <http://www.merck.com/mmpe/sec04/ch034/ch034b.html?qt=rheumatoid%20arthritis&alt=sh>.*
Barinaga, Marcia. Treating Arthritis with Tolerance Science; 361 1669-1670(1983).
Bendi et al. Purification and Charactenzation of a Collagen-degrading Protease from Porphyromonas gingivalis J Bic Chem 269: 599-606 (1994).
Bruckner et al p-HMW-Collagen. a minor collagen obtained from chick embryo cartilage without proteolytic treatment of the tissue Eur J Biochem 136: 333-339, (1983).
Cremer et at Collagen-Induced Arthritis in Rats: Antigen-specific Suppression of Arthritis and Immunity by intraveneously Injected Native Type II Collagen. J. of Immun. 131 (6) 2995-3000 (1983).
Darnell et al Molecular Cell Biology Scientific American Books, Inc New York, NY 1985.
Englert et al., Suppression of Type II Collagen-Induced Arthritis by th e Intraveneous Administration of Type II Collagen or its Constituent Peptide (II) CB Cellular Immunology 87: 357-365 (1984).
Fawcett. A Textbook of histology W B Saunders Co Philadelphia, PA (1986).
Knauper et al. Biochemical Characterization of Human Collagenase-3. J. Biol. Chem. 271. 1544-1550 (1996).
New Product Advertisement for "Hydrolyzed Collagen Beauty Supplement". Smarter Nails & Hair, Inc. Newport Beach, CA 92660 (1987).
Stryer. Collagen Has an Unusual Amino Acid Composition and Sequence. Biochemistry, Third Edition, W.H. Freeman and Co., New York, p. 262 (1988).
Trentham et al. Autoimmunity to Type II collagen: An Experimental Model of Arthritis. J. of Exq. Medicine 148: 857-868 (1977).
Trentham et al Effects of Oral Administration of Type II Collagen on Rheumatoid Arthritis. Science 261: 1727-1730 (1993).

* cited by examiner

*Primary Examiner*—Allison M. Ford
(74) *Attorney, Agent, or Firm*—Fish & Associates, PC (57) ABSTRACT

Hydrolyzed collagen type II powder compositions for inducing cartilage formation in an individual, method of preparing the compositions and use of the compositions in treating connective tissue disorder, replenishing skin viscoelasticity. The compositions are administered through an orally ingestible delivery medium for absorption into the gastrointestinal tract. The compositions are administered through a topical delivery medium for absorption into a dermis of the individual.

25 Claims, 5 Drawing Sheets

THERAPEUTIC COMPOSITION COMPRISING HYALURONIC ACID AND CHONDROITIN SULFATE AND METHOD OF MAKING SAME

CROSS-REFERENCE TO RELATED APPLICATIONS

The present application is a continuation application of application Ser. No. 10/870,841 filed on Jun. 17, 2004 now U.S. Pat. No. 7,091,180, which is a continuation of application Ser. No. 10/008,012 now issued U.S. Pat. No. 6,780,841 entitled HYALURONIC ACID AND CHONDROITIN SULFATE BASED HYDROLYZED COLLAGEN TYPE II AND METHOD OF MAKING SAME filed Nov. 13, 2001.

STATEMENT RE: FEDERALLY SPONSORED RESEARCH/DEVELOPMENT (Not Applicable)

BACKGROUND OF THE INVENTION

The present invention relates to hydrolyzed collagen type II powder compositions for inducing cartilage formation in an individual, a method of preparing the compositions and the use of the compositions in treating connective tissue disorder and replenishing skin viscoelasticity.

Studies have shown that collagen is a complex structural protein which provides strength and flexibility to skin, hair and nails. Collagen is an essential and major component of muscles, tendons, cartilage, ligaments, joints and blood vessels in the human body. There are three main types of collagen: I, II and III. Types I and III are primarily found in skin, tendon and bone. In contrast, type II is found predominantly in articular cartilage. Collagen is an unusual protein, in that the proportion of glycine residues is nearly one-third, which is unusually high in comparison to other typical proteins. Proline is also present to a much greater extent in collagen than in most other proteins. Moreover, collagen contains two amino acids, 4-hydroxyproline and 5-hydroxylysine, that are found in very few other proteins. The amino acid sequence of collagen is remarkably regular, nearly every third amino acid being glycine. In addition, the sequence glycine-proline-hydroxyproline recurs frequently. In contrast, globular proteins rarely exhibit regularities in their amino acid sequences (Stryer, L., *Biochemistry*, Third Edition, W.H. Freeman and Co., New York, 1988, pp. 262).

In 1986, collagen was sold for the first time in the United States for use as a food supplement. Collagen (a mixture of Types I and III) was extracted from calf skin tissue, hydrolyzed and prepared in powdered form for use as a dietary supplement. The composition was sold under the name "Hydrolyzed Collagen Beauty Supplement™" (Smarter Nails & Hair, Inc., Newport Beach, Calif.). In 1987, "Hydrolyzed Collagen Beauty Supplement Tablet™" (Smarter Nails & Hair, Inc., Newport Beach, Calif.) was sold which comprised collagen powder and 10 mg vitamin C compressed into 1,000 mg tablets.

U.S. Pat. No. 4,804,745 to Koepff et al. discloses agents containing collagen peptides produced by enzymatic hydrolysis for the treatment of degenerative joint diseases. These peptides can be obtained from animal skin, animal bones and other sufficiently purified connective tissue and have average molecular weights of between 30 and 45 kilodaltons.

U.S. Pat. No. 5,399,347 to Trentham et al. and Trentham et al. (*Science* 261:1727-1729, 1993) disclose the effective treatment of rheumatoid arthritis (RA) with water-soluble whole chick collagen type II or biologically active peptides derived therefrom. The mechanism by which the effect is believed to occur is via oral tolerization to autoantigens.

U.S. Pat. No. 5,364,845 to Henderson discloses a therapeutic composition and method for the protection, treatment and repair of connective tissue in mammals. This composition comprises glucosamine, chondroitin sulfate and manganese ascorbate. U.S. Pat. No. 5,587,363 to Henderson discloses a therapeutic composition and method for the protection, treatment and repair of connective tissue in mammals which includes aminosugars and glycosaminoglycans.

Another well known substance which aids in the rejuvenation and treatment of such ailments as connective tissue disorder is a substance known as Hyaluronic Acid (also known as "Hyaluronan" or "HA"). It is well known that the human body naturally contains such HA, as it is found in several parts of the body such as the soft connective tissue, the vitreous body of the eye, hyaline cartilage, synovial joint fluid, the dermis, and the epidermis. Within these parts of the body, HA acts as a lubricant between connective tissues of the skin, protects the joints by providing shock-absorption, and helps the body retain skin moisture. Over time however, as the body ages, the amount of HA present in the body deteriorates and the body may eventually develop one of several health problems, in part due to a decreased presence of HA. This effect is particularly apparent for those who are over the age of 50. Generally, the skin loses viscoelasticity, and wrinkles form ultimately as a result of this deficiency.

Due to the fact that HA is found in several different parts of the body, such a decrease in HA levels is associated with a great variety of disorders and ailments. For example, osteoarthritis patients experience decreased levels of HA in their synovial fluid. This has a detrimental effect on the joints because HA is primarily responsible for the lubricating and shock-absorbing effects of the synovial fluid. For this reason, researchers have theorized that the replacement of such lost HA may help osteoarthritis sufferers to rebuild damaged cartilage and to regain joint movement.

However, HA is not found exclusively in the human body. As a matter of fact, HA is found in most animals. For this reason, there has been substantial research conducted to extract HA from other sources so that humans may replenish the levels of HA that are lost over time. HA may be extracted from several sources such as from micro-organisms (Streptococcal cultures) through a fermentation process or from the isolation HA from rooster combs. Of these major sources, rooster combs produce HA having higher molecular weights. HA having a high molecular weight is too large to penetrate into the skin and the bloodstream and is therefore limited in its application. Generally, high molecular weight HA is used for eye surgery and cosmetics, specifically for creating a viscoelastic film to retain skin moisture and to block foreign substances.

For Osteoarthritis ("OA") patients, one method of relieving joint pain is via a therapy known as viscosupplementation. Viscosupplementation requires an intra-articular injection of HA to alleviate the pain associated with OA and allows the patient to regain function of the affected joints. The end result of such treatment is that the HA has an anti-inflammatory effect. Alternatively, the patient may use intra-articular glucocorticoid injections. The benefit of both injections are somewhat comparable but the common disadvantage to both therapies is the invasive nature of the injections.

Figure 2:
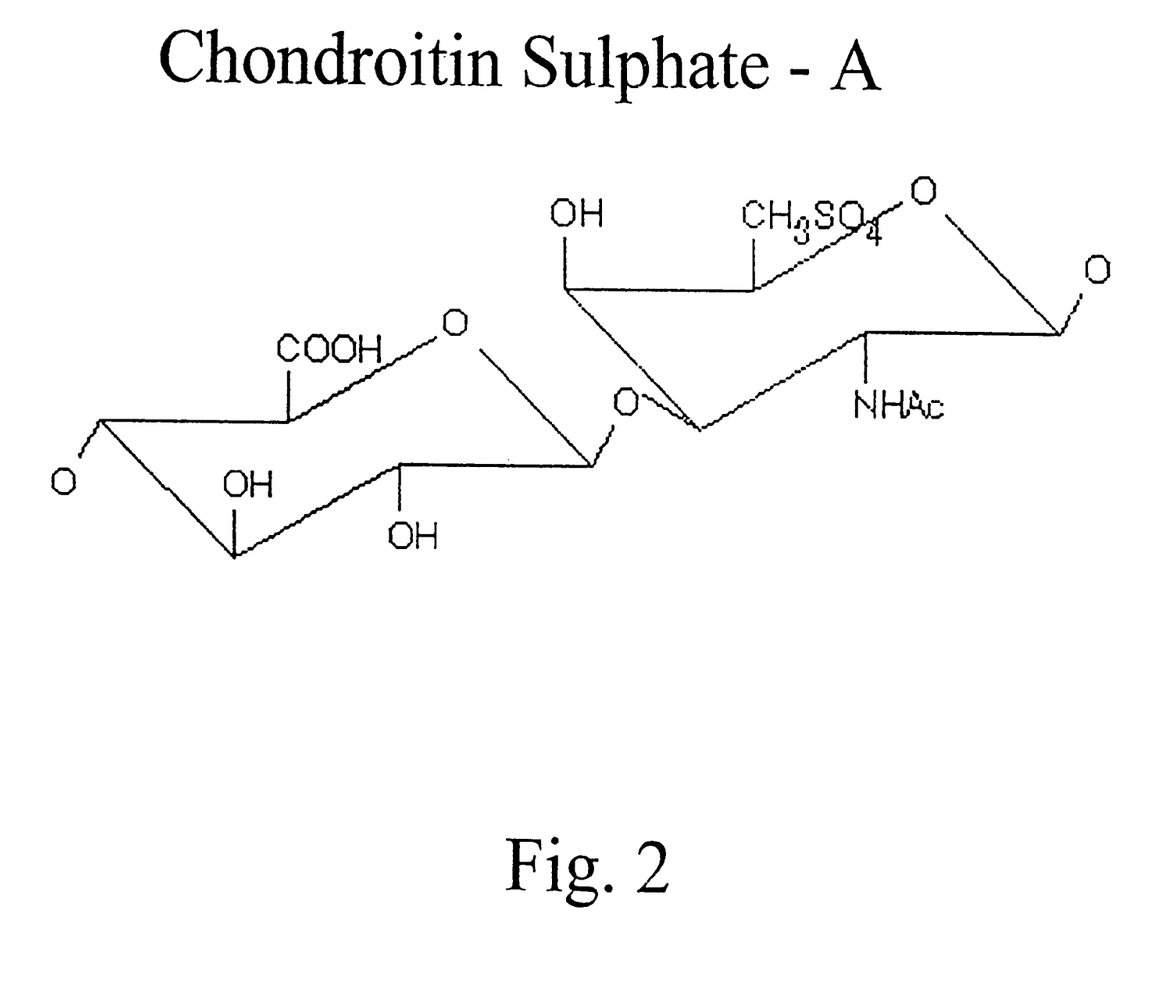
FIG. 2 is a molecular diagram showing Chondroitin Sulphate-A.
Figure 3:
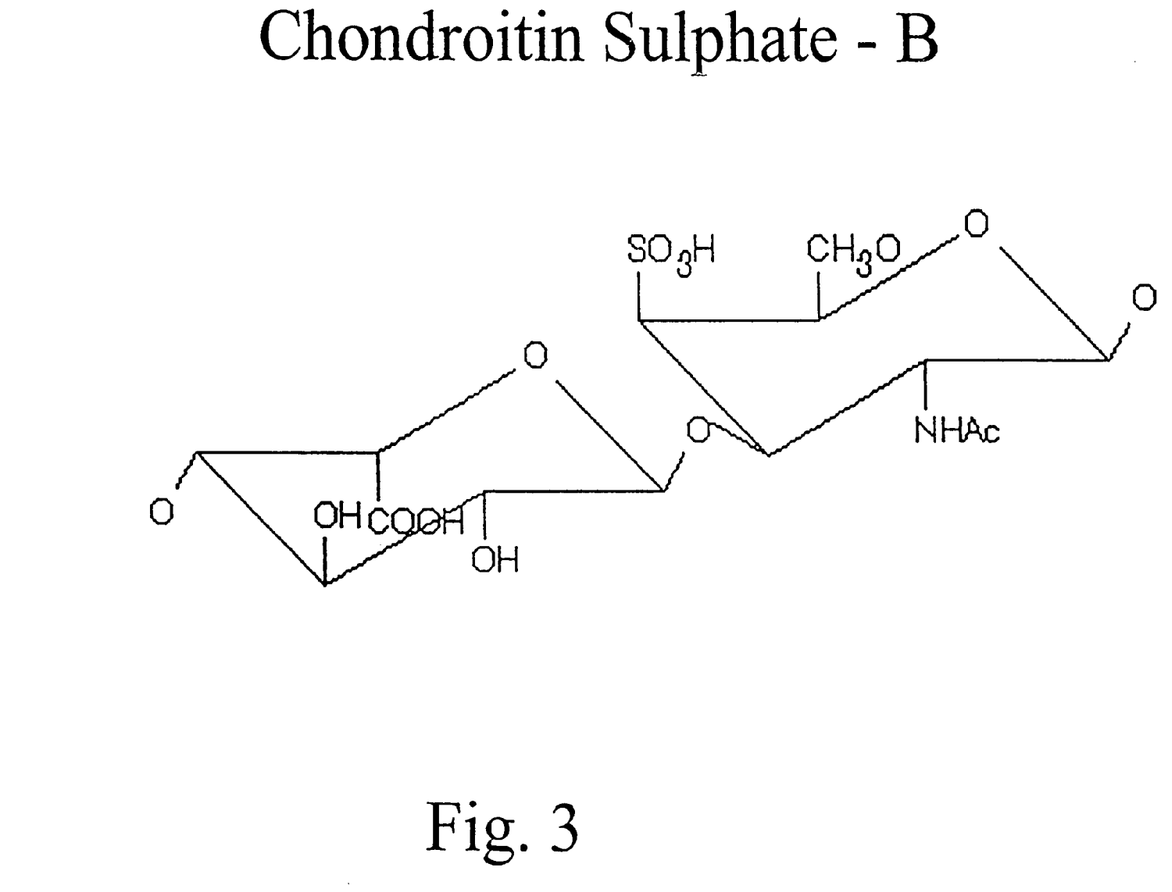
FIG. 3 is a molecular diagram showing Chondroitin Sulphate-B.
Figure 4:
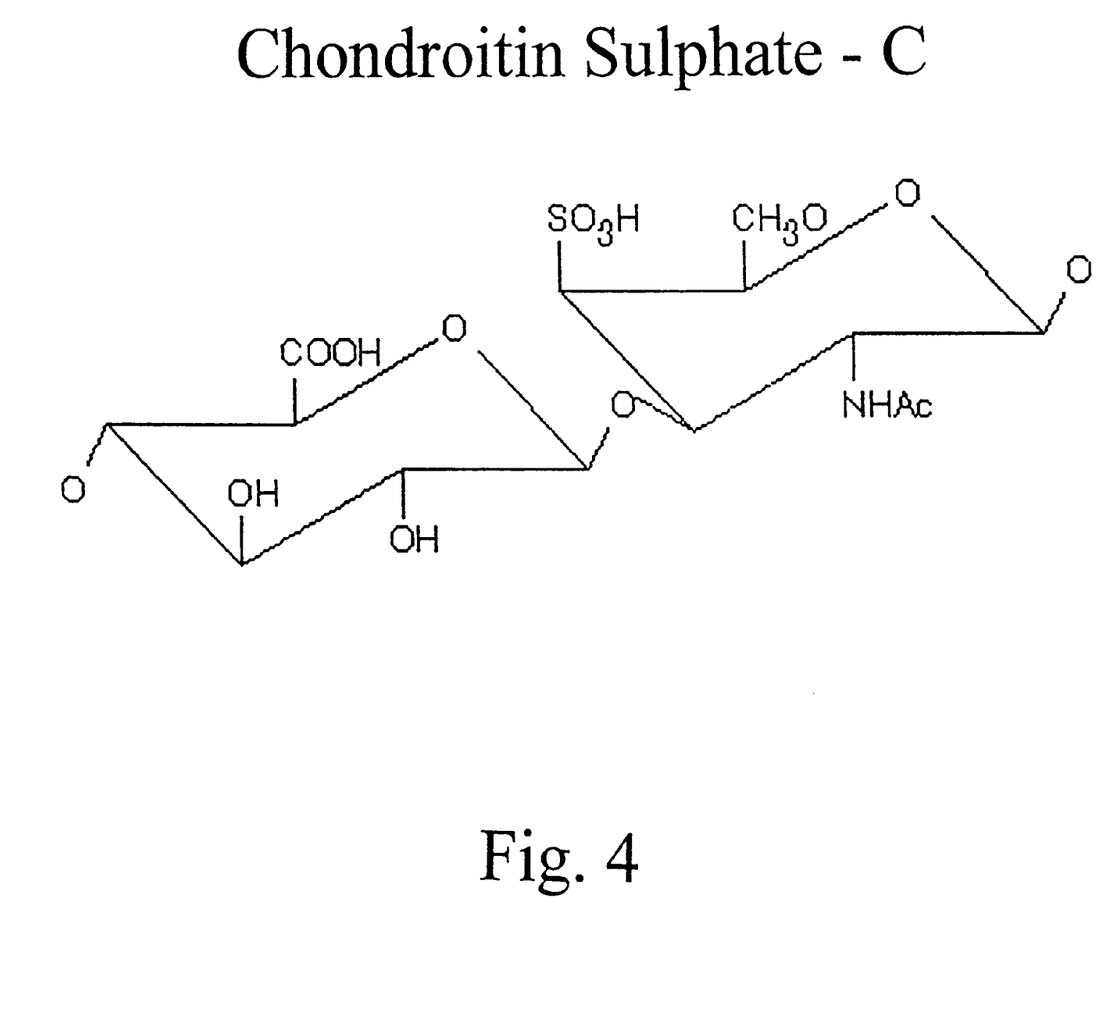
FIG. 4 is a molecular diagram showing Chondroitin Sulphate-C.
Figure 5:
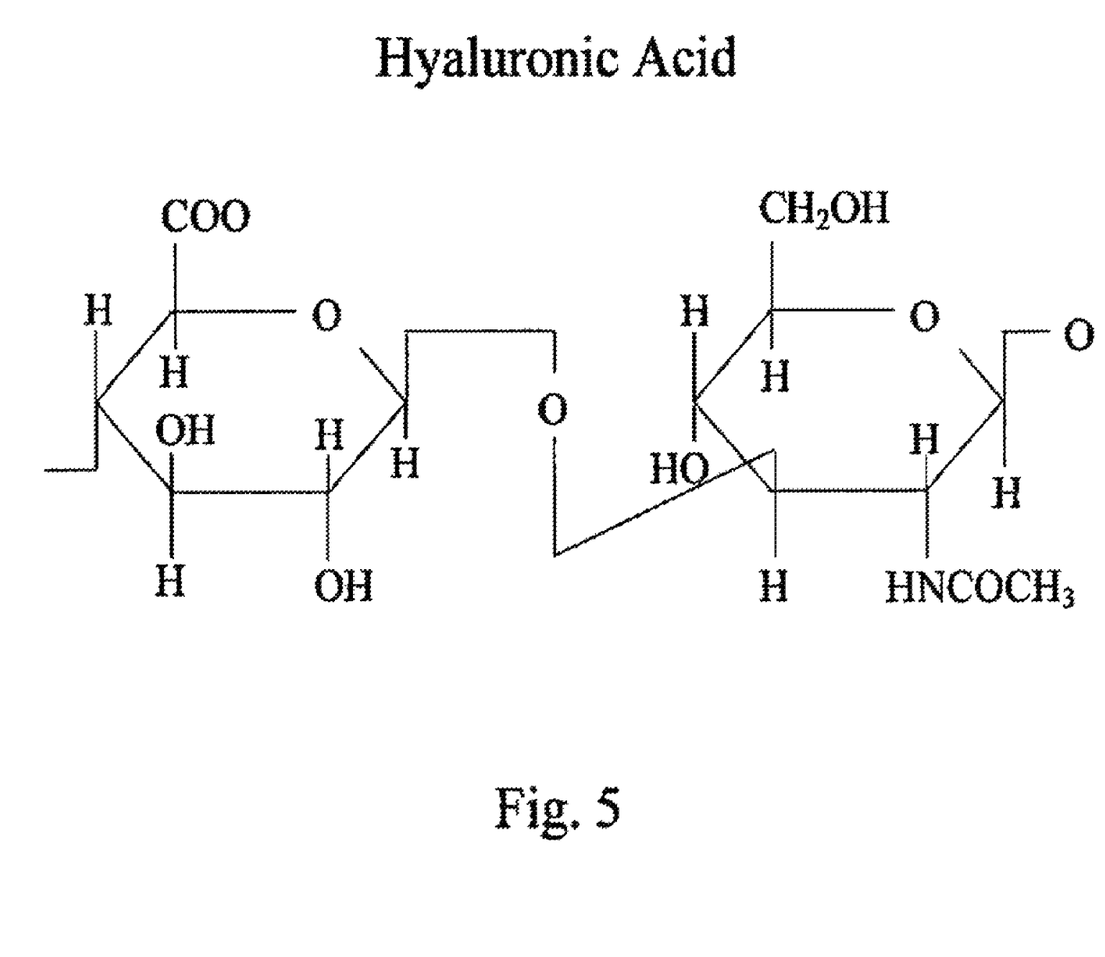
FIG. 5 is a molecular diagram showing Hyaluronic Acid.

Another constituent which alleviates pain in the joints and helps rebuild connective tissue is an endogenous Glycosaminoglycan ("GAG") called Chondroitin Sulfate ("CSA") which is composed of Glucuronic Acid+N-acetyl-D-galactosamine+Glucosamine Sulfate. Generally, CSA is a biological polymer derived from connective tissue. There are three types of Chondroitin Sulfate: Chondroitin Sulfate A ("CSA-A") (shown in FIG. 2) which is also known as chondroitin 6-sulphate, Chondroitin Sulfate B ("CSA-B") (shown in FIG. 3) which is also known as dermatan sulphate, and Chondroitin Sulfate C ("CSA-C") (shown in FIG. 4) which is also known as chondroitin 4-sulphate. The ratio of CSA-A to CSA-C declines in tandem with the progression of the aging process as does the content of CSA-B in the Dermis of the skin. In this respect, CSA levels are gradually depleted and such a decrease in CSA levels has a similar effect to a decrease in HA levels in that the shock-absorption and lubrication qualities are reduced. Thus, like HA, CSA is generally an important GAG for the maintenance of connective tissue.

Specifically, CSA-A has proven to be an effective antiinflammatory that improves blood circulation, prevents Ischemic Heart Disease, reduces incidences of heart attacks, reduces incidences of strokes, and is also effective in supporting connective joint tissue. Insofar as Chondroitin Sulfate helps prevent heart disease, this phenomenon is due to the inherent antithrombogenic or anticoagulant properties which prevent abnormal blood clots and reduce the incidence of strokes. CSA-B is found in the dermis of the skin and is also one of the constituents responsible for maintaining viscoelasticity of the skin. CSA-C inhibits Elastase, which is an enzyme that progressively degrades cartilage during the onset of Osteoarthritis.

Currently, Chondroitin Sulfate may be naturally ingested via seafood. For example, mussels, oysters and shark cartilage naturally contain Chondroitin Sulfate such that ingesting these types of foods may help replenish lost Chondroitin Sulfate over time. However, it is impractical to continually ingest seafood on a regular basis because some people are allergic to particular types of seafood, seafood is relatively expensive, and some simply do not like the taste of seafood. Additionally, several Chondroitin Sulfate nutritional supplements are being sold currently for treating connective joint tissue. Most of these supplements derive the Chondroitin Sulfate from bovine cartilage or velvet deer antler. In these forms, Chondroitin Sulfate is generally a difficult compound to digest in the gastrointestinal tract and the type of Chondroitin Sulfate derived from such animals is generally not very effective in absorbing into the bloodstream.

There is a need for non-invasive therapies in treating OA and other connective tissue disorders which may be treated with HA and a need for compositions capable of promoting repair of damaged connective tissue. The present invention addresses this need.

BRIEF SUMMARY OF THE INVENTION

One embodiment of the present invention is hydrolyzed collagen type II, the hydrolyzed collagen having an average molecular weight of between about 50 and 10,000 daltons. Preferably, the hydrolyzed collagen type II has an average molecular weight of about 5,500 daltons. In one aspect of this preferred embodiment, the collagen is obtained from chicken sternal cartilage. The hydrolyzed collagen type II preferably includes at least 20% depolymerized chondroitin sulphate and at least 10% hyaluronic acid. The collagen may be formed into an orally ingestible delivery medium or a topical delivery medium. The collagen is a low molecular weight, thereby allowing the orally ingestible delivery medium to readily absorb into the gastrointestinal tract of an individual while the topical delivery medium readily absorbs into the dermis of an individual.

The present invention also provides a method of inducing cartilage formation in an individual with a connective tissue disorder, comprising orally administering to the individual an effective daily cartilage-inducing amount of hydrolyzed collagen type II. The connective tissue disorder includes degenerative joint diseases, joint defects, osteoarthritis, polychondritis, vascular disease and cartilage injuries. Preferably, the effective daily amount is between about 500 and 5,000 mg. More preferably, the effective daily amount is between about 1,000 and 4,000 mg. Most preferably, the effective daily amount is between about 2,000 and 3,000 mg.

Another embodiment of the invention is a method of replenishing hyaluronic acid and chondroitin sulfate, restoring skin viscoelasticity, retaining skin moisture, healing wounds and improving the overall appearance of skin comprising topically administering to an individual, or other animal, a selectable amount of chicken sternal cartilage-derived material comprising hydrolyzed collagen type II having an average molecular weight of between about 50 and about 10,000 daltons. In this embodiment, the patient is given the option of applying as much or as little as desired to portions of the body as the individual sees fit (i.e., the eyes).

Still another embodiment of the invention is a method of preparing hydrolyzed collagen type II powder, comprising the following steps: cutting fresh chicken sternal cartilage to within not less than about 2 mm of the bone; suspending the cartilage in an aqueous solution; treating said cartilage with a proteolytic enzyme to form a hydrolysate, said proteolytic enzyme being capable of hydrolyzing collagen type II to fragments having an average molecular weight of between 50 to 10,000 daltons; sterilizing the hydrolysate; filtering the hydrolysate; concentrating the hydrolysate; and drying the hydrolysate to form a collagen type II powder. The method may further comprise the step of freezing the cartilage after the cutting step. Preferably, the aqueous solution is water. Advantageously, the enzyme is papain, ficin or bromelain. In one aspect of this preferred embodiment, the sterilizing step comprises heating the hydrolysate at 95° C. for about 30 minutes. Preferably, the drying step comprises spray drying. Preferably, the pH of the suspending and treating steps is between about 4 and 8.

DETAILED DESCRIPTION OF THE INVENTION

The present invention provides a hydrolyzed, denatured collagen type II composition, method for preparing the composition and use of the composition in the prevention, treatment and repair of cartilage defects. The method involves cutting fresh sternal cartilage from chicken carcasses and removing all meat therefrom. The sternal cartilage is cut, leaving a space of about two millimeters from the bone so as to not remove any bone fragments. This is critical to the purity of the final product because it avoids contamination of collagen type II with types I and III found in bone. Collagen type II contains the greatest concentration of proteoglycans, which help rejuvenate connective tissue joints. Therefore, maintaining a pure collagen type II compound ensures that the highest concentration of such proteoglycans. The fresh sternal cartilage is then promptly frozen and the remains of the chicken carcass are discarded. It is exclusively the sternal cartilage that is used for preparing the collagen type II powder. The chicken sternal cartilage is processed according to good manufacturing procedures (GMP).

Other contemplated sources of collagen type II are mammalian cartilage (e.g. bovine, porcine and avian) and shark fins. However, such forms of collagen type II are generally less effective in absorbing into the gastrointestinal tract. On the other hand, the present invention naturally contains depolymerized chondroitin sulfate. This particular form of chondroitin sulfate derived from the chicken sternal cartilage absorbs into the gastrointestinal tract approximately three to five times better than traditional bovine derived forms which may not be depolymerized. In this respect, the depolymerized chondroitin sulfate is broken down into its individual monomers for an increased ability to absorb into the gastrointestinal tract, thereby increasing the blood concentrations of glycosaminoglycans rich in hydrolyzed collagen type II. Preferably, the present invention includes 20-25% depolymerized chondroitin sulfate, a high concentration of this easily absorbable constituent. However, this depolymerized chondroitin sulfate also provides for absorption into the body via other means. For example, the depolymerized chondroitin sulfate in the present invention may absorb into the skin when applied topically to replenish CSA-C in the dermis.

Similarly, the hyaluronic acid present in the collagen replenishes lost levels of such hyaluronic acid in the body by supplementing the synovial joint fluid, cartilage, eyes, skin tissue, connective tissue, nails, and other parts of the body which gradually lose hyaluronic acid over time. The collagen having the hyaluronic acid also provides structural support to joints, promotes new cartilage synthesis, helps heal wounds and is useful in a myriad of other applications where hyaluronic acid and chondroitin sulfate is generally found within the human body, or animal body. Advantageously, because the collagen is a low molecular weight, the hyaluronic acid contained in the collagen is capable of absorbing into the gastrointestinal tract via oral delivery mediums and can absorb into the skin when applied topically. Thus, hyaluronic acid is also capable of reaching the corium layers of the dermis via oral ingestion. In this respect, the hydrolyzed collagen type II and its unique low molecular weight properties allow for the hyaluronic acid, chondroitin sulfate, glucosamine sulfate, cartilage matrix glycoprotein (CMGP), and other glucosaminoglycans to all absorb into the gastrointestinal tract via oral delivery mediums and into the skin via topical delivery mediums.

Figure 1:
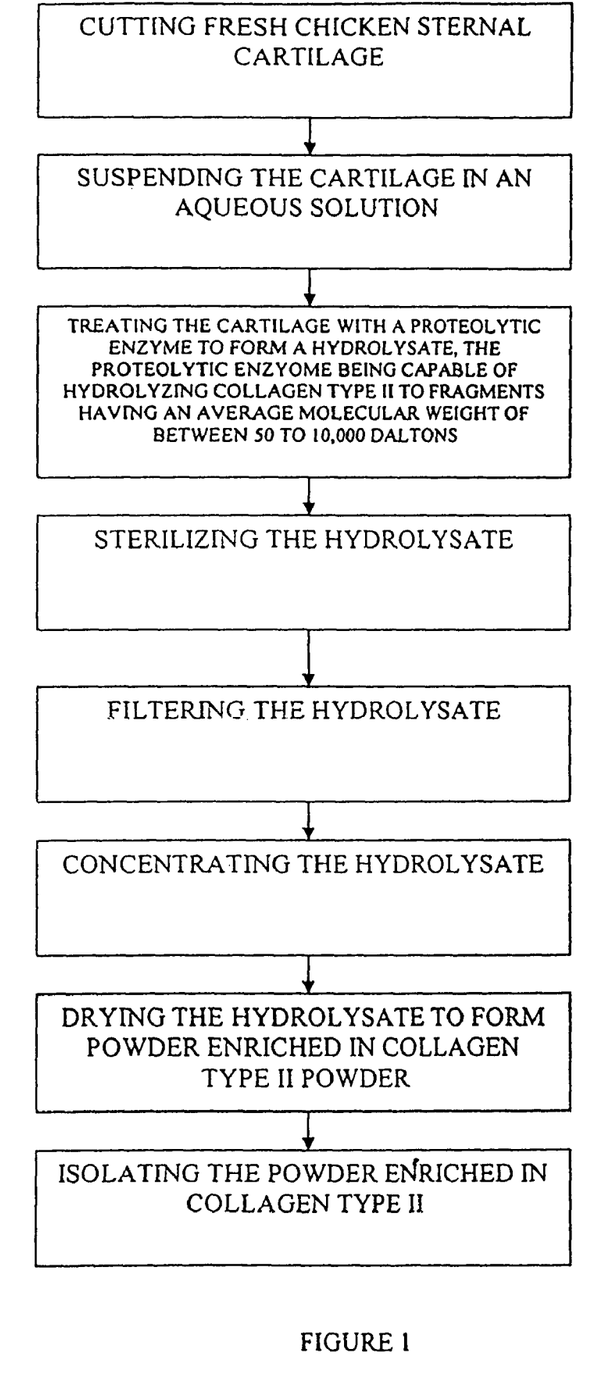
FIG. 1 is a schematic diagram of the process for preparing the hydrolyzed collagen type II powder of the invention.

The production of hydrolyzed collagen type II in powdered form is shown in FIG. 1. Whole cartilage is suspended in an aqueous solution, preferably water for about one hour at about 35° C. at a pH of between about 4 and 8. In a preferred embodiment, the pH is between about 6 and 7. In a more preferred embodiment, the pH is about 6.5. The water is removed, and the cartilage is incubated with one or more proteases obtainable from a natural source (i.e. papain, ficin, bromelain) for between about 2 and 10 hours, preferably about 6 hours, at about 35° C.-55° C. at a pH of between about 4 and 8 to form a hydrolysate. The pH will depend on the pH optimum of the particular enzyme(s) used for the hydrolysis and are well known to one of ordinary skill in the art. The hydrolysate is then sterilized for about 30 minutes at a temperature between about 95° C. and 105° C. The sterilized hydrolysate is filtered through diatomaceous earth, concentrated, preferably under vacuum, dried to form a powder and packed. Other filtration methods are contemplated, including vacuum filtration. In a preferred embodiment, the hydrolyzed collagen type II is spray dried using a size 56 pressure nozzle into a heat tunnel. The final particle size and mesh are adjusted to 0.46 g/cc, yielding a fine powder. The powder is packed in a 40 kg drum with a plastic bag liner. The powder is water soluble.

The average molecular weight of the final product is between 50 and 10,000 daltons, preferably 5,500 daltons. The moisture content is between 5% and 7%. The final product is high in mucopolysaccharides, particularly chondroitin sulfate and glucosamine sulfate. Such mucopolysaccaraides are major constituents in providing shock-absorption and lubrication in the connective tissue joints. The product has 375 calories per 100 grams, contains 67% protein (12.1% total nitrogen), 18% carbohydrate and 0.1% fat. The amino acid composition of the hydrolysate differs substantially from typical collagens and is shown in Table 1. Hydroxyproline is low, hydroxylysine is absent and tryptophan is low. The low molecular weight and high amino acid composition promote optimal assimilation of the peptides.

TABLE 1

| Amino acid composition of hydrolyzed collagen type II | |
|---|---|
| Amino acid | g/100 g product |
| arginine | 4.42 |
| histidine | 2.05 |
| isoleucine | 1.90 |
| leucine | 4.20 |
| lysine | 3.54 |
| methionine | 1.38 |
| phenylalanine | 2.14 |
| threonine | 2.60 |
| tryptophan | 0.37 |
| alanine | 4.51 |
| asparagine/aspartic acid | 5.29 |
| cystine | 0.46 |
| glutamine/glutamic acid | 8.75 |
| glycine | 8.93 |
| hydroxyproline | 3.90 |
| proline | 5.25 |
| serine | 2.45 |
| tyrosine | 1.16 |
| valine | 2.43 |

A test analysis of the hydrolyzed collagen yields results which indicate that at least 20% of depolymerized chondroitin sulfate is present in the collagen. Additionally, at least 10% of hyaluronic acid is also found therein. However, because the collagen is extracted from a natural source (i.e. chicken sternum), the actual percentage of depolymerized chondroitin sulfate and hyaluronic acid may vary. The highest concentration of depolymerized chondroitin sulfate and hyaluronic acid obtainable is preferred.

TABLE 2

| Test Results of Hydrolyzed Collagen Type II | |
|---|---|
| | Specifications |
| Typical analysis | |
| Purity | 100% |
| Solubility | Water-Soluble |
| Chondroitin Sulfate | ~20.0% |

TABLE 2-continued

Test Results of Hydrolyzed Collagen Type II

| | Specifications |
|---|---|
| Hyaluronic Acid | ~10.0% |
| Other Proteoglycans | ~3.0% |
| Collagen Type II Protein | ~62.7% |
| Nitrogen | 12.1% |
| Fat | 0.0% |
| Loss on Drying | <8% |
| Heavy Metals | <5 ppm |
| Ash | 8.3% |
| Calcium | 530 mg/100 gms |
| Magnesium | 161 mg/100 gms |
| Potassium | 1961 mg/100 gms |
| Microbiological Analysis | |
| Standard Plate Count | <1000 gms |
| E. Coli | Negative |
| Salmonella | Negative |
| Physical Analysis | |
| Appearance | Off white/yellow fine powder |
| Odor | Characteristic |
| Particle Size | >100 mesh |

When taken orally by an individual with a connective tissue disorder, hydrolyzed collagen type II helps build cartilage and significantly improves the disorder. The lost levels of HA, CSA-A, CSA-B, and CSA-C in the joints are replenished via ingestion into the gastrointestinal tract. Furthermore, oral ingestion of the hydrolyzed collagen type II helps contribute to the wound healing process due to the chondroprotective nature of the collagen's composition.

"Oral" administration includes oral, enteral or intragastric administration. The hydrolyzed collagen type II of the invention can be used to treat, for example, degenerative joint diseases (i.e. rheumatoid arthritis, joint defects, osteoarthritis, polychondritis, vascular disease, cartilage injuries, silicone poisoning due to ruptured breast implants, autoimmune diseases involving connective tissue autoantibodies (i.e. rheumatoid arthritis), progressive myopia, Menier's disease and any other connective tissue disorder which would benefit from increased synthesis of cartilage. The hydrolyzed collagen type II also significantly reduces sun-induced skin wrinkles.

By extracting HA from chicken sternal cartilage, a low molecular weight HA may be obtained by hydrolysis after such extraction. This distinction is crucial because the beneficial therapeutic activity of HA is mostly dependent upon the molecular weight of HA. Due to the low molecular weight of the HA found in the hydrolyzed collagen type II, the hydrolyzed collagen type II readily absorbs into the gastrointestinal tract and allows the rejuvenating constituents of HA and CSA to restore viscoelasticity to the skin, protect connective tissues, promote cartilage synthesis, retain skin moisture, heal wounds and improve the overall appearance of skin. In its oral form, the hydrolyzed collagen type II is capable of reaching the corium layers of the skin which typically cannot be reached by topical applications.

For oral administration as a nutritional supplement, therapeutic or prophylactic agent, the hydrolyzed collagen type II of the invention may be provided as a dispersible powder or granule, tablet, aqueous or oil suspension, emulsion, hard or soft capsule, syrup or elixir. Advantageously, the ability to provide the hydrolyzed collagen type II in such a variety of forms allows the invention to be used by itself or in conjunction with several different applications.

The low molecular weight of the hydrolyzed collagen type II allows the powder form to be integrated into topical gels. In this respect, the gel may be applied directly to the skin and ultimately, the collagen readily absorbs into the skin. Absorption directly into the skin provides the advantage of moisturizing the skin, maintaining fluid balance in the cells of the skin and providing a thin layer of viscoelastic protective film which keeps foreign substances from attacking the skin. Additionally, the film retains water and moisturizes the skin in much the same way that hyaluronic acid does in the intercellular matrix of dermal connective tissue. Ultimately such application helps the skin appear younger, reduces the effects of aging upon the skin, and accelerates the wound healing process when the collagen is applied to wounds. Additionally, topical application provides the advantage of a targeted solution to where the consumer needs it the most. For example, the topical collagen user's predominate purpose may be to rejuvenate the skin and restore viscoelasticity to improve the overall appearance of the skin. Such a user may then apply the topical collagen to the desired parts of the body, such as under the eyes, to concentrate on rejuvenating that particular area. A topical form may also be used for administering the collagen to wounds for reducing the appearance of scarring and accelerating the overall wound healing process. On the other hand, an orally ingestible form provides the advantage of allowing a total body rejuvenation wherein the collagen restores hyaluronic acid and chondroitin sulfate constituents to parts of the body which are deficient in these chemicals.

As a cosmetic, the collagen may be integrated with existing facial cosmetics, such as foundation, concealer, and lipstick as an additive which works invisibly to replenish the lost constituents. In this respect, the cosmetic user may apply the daily cosmetics as usual without the requirement of an additional moisturizer due to the collagen's ability to help retain natural skin moisture. Furthermore, it is contemplated that the collagen may be used in conjunction with other typical consumer products where skin moisturizing is also useful. For example, some soaps include a moisturizer as an ingredient to counteract any drying effects detergents may have on the skin. The collagen may be used with a moisturizer to also counteract such effects while simultaneously replenishing lost levels of HA and CSA.

The hydrolyzed collagen type II may serve as an ingredient of a product medication manufactured to facilitate healing of wounds and injuries. In this regard, such product medication, which incorporates the hydrolyzed collagen type II as one of its ingredients, may be directly medicated on areas of skin where the wound occurs. Additionally, the collagen may be integrated into an orally ingestible form of wound healing medication by absorbing into the gastrointestinal tract. Of course, sufficient quantity should be applied to promote a healing process of the wound.

Specifically, the hydrolyzed collagen type II of the present invention may be conformed to provide topical applications so as to accelerate healing of wounds and injuries associated with the diseases/disorders described above (e.g., cartilage injuries, hepatitis, decubititis). In this respect, when a wound heals, the fibroplasts secrete glycosaminoglycans such that a hydrophilic matrix is formed. The hydrophilic property of the hydrolyzed collagen may then provide a greater degree of epithelialization. The increased presence of such glycosaminoglycans assists the fibroblasts which are continually moving and replicating during the wound healing process. Thus, the overall process for accelerating the healing of cutaneous wounds is accelerated by applying the collagen to the wound. In the same respect, the same properties of the collagen assist in plastic surgery applications for burn victims. Applying the collagen to wounds, skin graft sites, and skin donor sites may reduce inflammation, reduce the incidence of scarring, and also increase the overall healing process.

Compositions intended for oral use may be prepared according to any method known in the art for the manufacture of pharmaceutical compositions and such compositions may contain one or more of the following agents: sweeteners, flavoring agents, coloring agents and preservatives. The sweetening and flavoring agents will increase the palatability of preparation. Tablets containing the hydrolyzed collagen type II in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed. The use of enteric coatings is also contemplated.

Formulations for oral use may also be presented as hard gelatin capsules wherein the active ingredient is mixed with an inert solid diluent, for example calcium carbonate, calcium phosphate or koalin, or as soft gelatin capsules wherein the active ingredient is mixed with water or an oil medium, such as peanut oil, liquid paraffin or olive oil.

Aqueous suspensions may contain the hydrolyzed collage type II of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring agent and/or a coloring agent.

The hydrolyzed collagen type II powder may be mixed with other ingestible forms and consumed in solid, semi-solid solution, suspension or emulsion form. It may also be mixed in conjunction or alternatively with pharmaceutically acceptable carriers, flavor enhancers, water, suspending agents and emulsifying agents. In a preferred embodiment, the hydrolyzed collagen type II powder is mixed with a citrus juice such as orange, grapefruit or tangerine due to the promotion of connective tissue formation by ascorbic acid. The hydrolyzed collagen may also be provided in tablet form in admixture with ascorbic acid.

For use as a nutritional supplement, prophylactic or therapeutic agent, the hydrolyzed collagen is orally administered in a daily dosage of between about 500 mg and 5,000 mg. More preferably, it is administered in a daily dosage of between about 2,000 mg and 4,000 mg. Most preferably, it is administered in a daily dosage of between about 2,000 and 3,000 mg per day. The hydrolyzed collagen type II powder may be formulated into tablets which range from 300 mg to 1,000 mg per tablet. In a preferred embodiment, the hydrolyzed collage type II powder is formulated into 500 mg tablets and 4-6 tablets are taken daily. In another preferred embodiment, the tablets are taken on an empty stomach with a beverage containing vitamin C.

In another preferred embodiment, the hydrolyzed collagen type II powder is mixed with water or a citrus juice prior to ingestion. The preparations described above can be taken indefinitely by individuals affected by connective tissue disorders or by healthy individuals as a preventative agent. If desired, an individual with such a disorder can take the preparation until no further improvement is noted in the disorder.

It is contemplated that application of the medication may be accomplished by wiping using sterile gloves, applying with appropriate devices, spray, painting, or other means to produce a continuous adhesive film on the wound. If additional support for the wound is required, bandages, splints, other medication dispensing devices, prosthetic devices or any other devices may be applied in conjunction therewith.

In addition, the hydrolyzed collagen type II of the present invention may further be adhered as a preventive remedy. For instance, like many other ingredients in the marketplace, the hydrolyzed collagen type II can be subjected to cosmetic applications used for anti-aging purposes. More particularly, as the hydrolyzed collagen type II can help reduce sun-induced skin wrinkles, it may therefore be integrated into an anti-aging cosmetic as one of its essential ingredients. As such, the hydrolyzed collagen type II of the present invention can be utilized in a variety of exemplary manners due to its primary inherent characteristic of inducing cartilage formation.

The above detailed description of the invention is set forth solely to assist in understanding the invention. It is to be understood that variations of the invention, including all equivalents now known or later developed, are to be considered as falling within the scope of the invention, which is limited only by the following claims.

What is claimed is:

1. A method of preparing a hyaluronic acid-containing supplement, comprising:
   hydrolyzing an animal product under conditions that produce a composition containing hydrolyzed type II collagen having an average molecular weight of between about 50 and about 10,000 daltons and at least 10% hyaluronic acid;
   obtaining test results showing that the composition contains at least 10% hyaluronic acid; and
   forming the composition into a supplement that is deliverable to the body of a subject, thereby producing a hyaluronic acid-containing supplement.

2. The method of claim 1, wherein the hydrolyzed composition further contains at least 20% chondroitin sulfate.

3. The method of claim 1, wherein the animal product is a chicken sternum.

4. The method of claim 1, wherein the animal product comprises a cartilaginous portion of a bird.

5. The method of claim 4, wherein the bird is a chicken.

6. The method of claim 1, wherein the animal product comprises at least one of hyaline and articular cartilage.

7. The method of claim 1, wherein the animal product comprises cartilaginous tissue of at least one of a cow, a pig and a shark.

8. The method of claim 1, wherein the step of hydrolyzing comprises heat hydrolyzing the animal product.

9. The method of claim 1, wherein the step of hydrolyzing comprises enzymatically hydrolyzing the animal product.

10. The method of claim 1, further comprising the step of at least partially dehydrating the hyaluronic acid-containing supplement.

11. The method of claim 1, further comprising the step of spray drying the hyaluronic acid-containing supplement.

12. The method of claim 1, wherein the step of forming the composition into a supplement comprises forming the composition into a tablet or capsule, wherein each tablet or capsule comprises between 300 mg and 1,000 mg of hydrolyzed type II collagen.

13. The method of claim 12, wherein each tablet or capsule contains 500 mg of hydrolyzed type II collagen.

14. The method of claim 1, wherein the hyaluronic acid-containing supplements contain an amount of hydrolyzed type II collagen such that a subject may be provided with a daily amount of 500 mg to 5,000 mg of hydrolyzed type II collagen from said supplements.

15. The method of claim 1, wherein the step of forming the composition into a supplement comprises forming the composition into a further comprising the step of packaging the supplement including the composition as dispersible powder, a granule, an aqueous suspension, an oil suspension, an emulsion, a soft capsule, a syrup or an elixir.

16. A method of administering collagen to an individual, comprising:
hydrolyzing an animal product under conditions that produce a composition containing hydrolyzed type II collagen having an average molecular weight of between about 50 and about 10,000 daltons and at least 10% hyaluronic acid;
obtaining test results showing that the composition contains at least 10% hyaluronic acid;
forming the composition into an oral supplement; and
orally administering the supplement to the individual.

17. The method of claim 16, wherein the individual has sun-induced wrinkles and the method reduces said sun-induced wrinkles.

18. The method of claim 16, wherein the step of forming the composition into an oral supplement comprises mixing the composition with a part of a functional food.

19. The method of claim 16, wherein the composition further comprises chondroitin sulfate.

20. The method of claim 1, wherein the step of forming the composition into a supplement comprises integrating the composition as part of a skin care product.

21. The method of claim 1, wherein the step of forming the composition into a supplement comprises integrating the composition as part of a cosmetic.

22. The method of claim 1, wherein the step of forming the composition into a supplement comprises integrating the composition as part of a moisturizer.

23. The method of claim 1, wherein the step of forming the composition into a supplement comprises integrating the composition as part of an anti-aging cosmetic.

24. The method of claim 1, wherein the step of forming the composition into a supplement comprises integrating the composition as part of a topical delivery medium.

25. The method of claim 16, wherein the individual has a connective tissue disorder selected from the group consisting of a degenerative joint disease, a joint defect, osteoarthritis, polychondritis, a cartilage injury, and combinations thereof; and
wherein the step of orally administering the supplement to the individual comprises orally administering an effective daily cartilage-inducing amount of the composition.

* * * * *